United States Patent
Kawano et al.

(10) Patent No.: US 9,188,538 B2
(45) Date of Patent: Nov. 17, 2015

(54) RAMAN MICROSCOPE AND RAMAN SPECTROMETRIC MEASURING METHOD

(75) Inventors: Shogo Kawano, Suita (JP); Taisuke Ota, Osaka (JP); Minoru Kobayashi, Osaka (JP)

(73) Assignee: Nanophoton Corporation, Osaka (JP)

( * ) Notice: Subject to any disclaimer, the term of this patent is extended or adjusted under 35 U.S.C. 154(b) by 0 days.

(21) Appl. No.: 14/124,269

(22) PCT Filed: Jun. 6, 2012

(86) PCT No.: PCT/JP2012/064577
§ 371 (c)(1),
(2), (4) Date: Dec. 6, 2013

(87) PCT Pub. No.: WO2012/169539
PCT Pub. Date: Dec. 13, 2012

(65) Prior Publication Data
US 2014/0132955 A1     May 15, 2014

(30) Foreign Application Priority Data
Jun. 7, 2011 (JP) .................. 2011-127217

(51) Int. Cl.
*G01J 3/44*     (2006.01)
*G01N 21/65*    (2006.01)
*G01J 3/02*     (2006.01)

(52) U.S. Cl.
CPC .............. *G01N 21/65* (2013.01); *G01J 3/0218* (2013.01); *G01J 3/0224* (2013.01); *G01J 3/44* (2013.01); *G01J 2003/4424* (2013.01)

(58) Field of Classification Search
CPC ............... G01N 21/65; G01N 21/658; G01N 2021/656; G01J 3/02; G01J 3/44
USPC .............................................. 356/301, 72–73
See application file for complete search history.

(56) References Cited

U.S. PATENT DOCUMENTS 6,560,478 B1 * 5/2003 Alfano et al. ................ 600/473
7,064,329 B2 * 6/2006 Webber .................... 250/339.12
(Continued)

FOREIGN PATENT DOCUMENTS

JP    11-295148     10/1999
JP    2003-241101   8/2003
(Continued)

OTHER PUBLICATIONS

International Search Report issued Jul. 17, 2012 in International Application No. PCT/JP2012/064577.
(Continued)

*Primary Examiner* — Abdullahi Nur
(74) *Attorney, Agent, or Firm* — Wenderoth, Lind & Ponack, L.L.P.

(57) ABSTRACT

A Raman microscope and a Raman spectrometric measuring method achieve measurements with high wavenumber resolution. The Raman microscope includes a pump light source for emitting pump light as continuous light; a relaxation light source for emitting relaxation light to induce stimulated emission in a sample; a dichroic mirror for irradiating the relaxation light and the pump light to the sample; a spectrograph for spectrally separating Raman scattered light generated in the sample; and a detector for detecting the Raman scattered light spectrally separated in the spectrograph.

18 Claims, 6 Drawing Sheets

(56) References Cited

U.S. PATENT DOCUMENTS

| | | |
|---|---|---|
| 8,290,004 B2 | 10/2012 | Kakui |
| 8,432,543 B2* | 4/2013 | Frankel ............... 356/301 |
| 8,487,271 B2 | 7/2013 | Yokoi et al. |
| 2001/0045529 A1 | 11/2001 | Iketaki et al. |
| 2007/0088219 A1* | 4/2007 | Xie et al. ............... 600/473 |
| 2008/0007716 A1 | 1/2008 | Igarashi |
| 2010/0046039 A1* | 2/2010 | Xie et al. ............... 358/471 |
| 2010/0067102 A1* | 3/2010 | Yokoi et al. ............ 359/385 |
| 2010/0272136 A1 | 10/2010 | Kakui |
| 2011/0282166 A1* | 11/2011 | Chen et al. ............. 600/306 |

FOREIGN PATENT DOCUMENTS

| | | |
|---|---|---|
| JP | 2006-58477 | 3/2006 |
| JP | 2007-71606 | 3/2007 |
| JP | 2009-258030 | 11/2009 |
| JP | 2010-15026 | 1/2010 |
| JP | 2010-92002 | 4/2010 |
| JP | 2010-258272 | 11/2010 |

OTHER PUBLICATIONS

Stefan W. Hell and Jan Wichmann, "Breaking the diffraction resolution limit by stimulated emission: stimulated-emission-depletion fluorescence microscopy", Optics Letters, vol. 19, No. 11, Jun. 1, 1994, pp. 780-782.

Extended European Search Report issued Jan. 26, 2015, in corresponding European Application No. 12796263.7.

* cited by examiner

RAMAN MICROSCOPE AND RAMAN SPECTROMETRIC MEASURING METHOD

BACKGROUND OF THE INVENTION

1. Technical Field

The present invention relates to a Raman microscope and a Raman spectrometric measuring method, and in particular, more specifically, it relates to a Raman microscope and a Raman spectrometric measuring method, in which Raman scattered light from a sample is spectrally separated.

2. Background Art

Raman spectroscopy, particularly Raman spectroscopy making use of Raman scattering as a linear optical process, has hitherto been used. In the Raman spectroscopy, monochromic light such as laser light is irradiated to a sample, and scattered light is spectrally separated by a spectrograph or the like. The spectrally separated light is then observed with an imaging device such as a CCD to obtain a Raman spectrum. Raman image has also widely been obtained by Focusing laser light and scanning the relative position between the sample and the laser spot.

PRIOR ART DOCUMENTS

Patent Documents

Patent Document 1: Japanese Patent Laid-open Publication (Kokai) No. 2009-258030
Patent Document 2: Japanese Patent Laid-open Publication (Kokai) No. 2007-71606
Patent Document 3: Japanese Patent Laid-open Publication (Kokai) No. 2010-92002

Non-Patent Documents

Non-Patent Document 1: Hell, S. W. and J. Wichmann (1994), "Breaking the diffraction resolution limit by stimulated emission," Opt. Lett. 19(11): 780-782.

SUMMARY OP THE INVENTION

Problems to be Solved by the Invention

Figure 11:
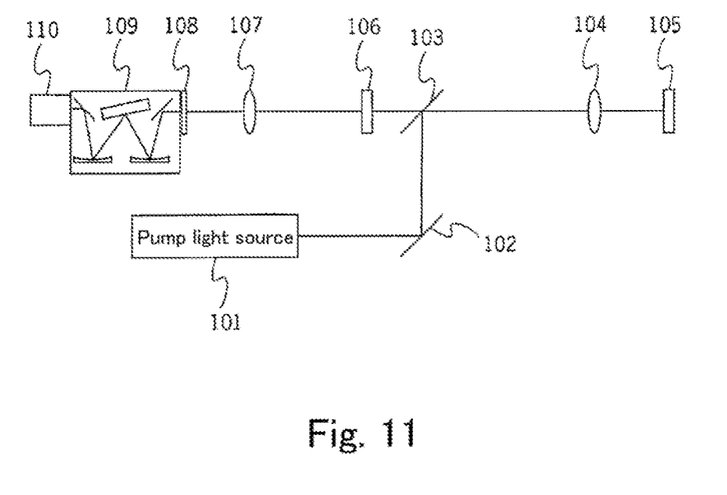
FIG. 11 is a diagram showing one example of the conventional Raman microscope optical systems.

The optical system of a conventional Raman microscope is shown in FIG. 11. Pump light from a pump light source 101 is introduced into a sample 105 through a mirror 102, a dichroic mirror 103, and an objective lens 104. Raman scattered light from the sample 105 is introduced onto a spatial filter 108 through the objective lens 104, the dichroic mirror 103, a notch filter 106, and a lens 107. The Raman scattered light passing through a spatial filter 108 is introduced into a spectrograph 109. The Raman scattered light spectrally separated by the spectrograph 109 is detected by a detector 110.

Figure 12:
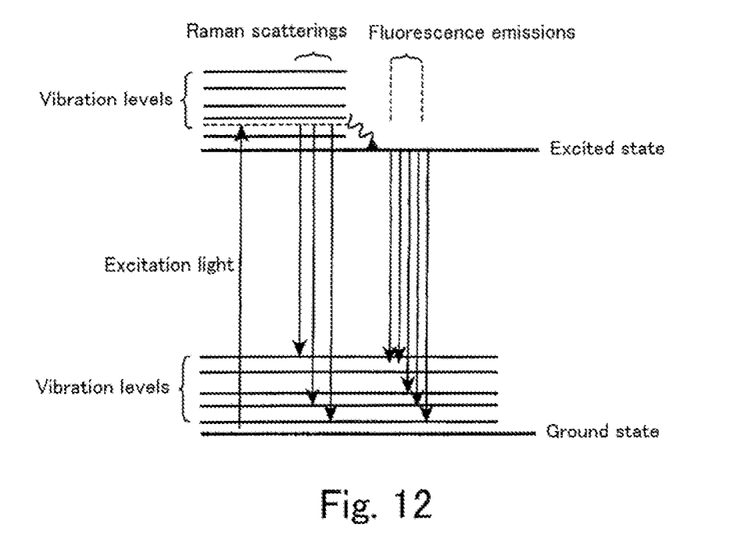
FIG. 12 is a Jablonski diagram of Raman scattering and fluorescence emission.

In the Raman spectroscopy, the measurement of Stokes Raman scattering is achieved by observation of Raman spectra in the range of wavelengths longer than the wavelength of irradiating light. As shown in FIG. 12, such observation may involve fluorescence emission depending on the types of irradiating light and sample. Fluorescence emission is caused at wavelengths longer than the wavelength of irradiating light. For this reason, Stokes Raman scattering spectra may overlap fluorescence spectra.

Fluorescence emission intensity is proportional to the product of irradiating light intensity, absorption cross-section, and quantum efficiency. Stokes Raman scattering emission intensity is proportional to the product of irradiating light intensity and Raman scattering cross-section. In this regard, the value of Raman scattering cross-section is smaller than the value of molecular absorption cross-section, and in general, fluorescence emission intensity becomes higher than Raman scattering intensity. For this reason, it is difficult to make Raman observation for samples that emit strong fluorescence. In the past, methods with optical processes that have higher efficiency than fluorescence have been used to make the effect of fluorescence relatively smaller, such as nonlinear Raman spectroscopy, coherent anti-Stokes Raman scattering or stimulated Raman scattering.

Alternatively, to solve part of such problems, a method of removing the influence of fluorescence from Raman spectra is disclosed (Patent Documents 1 and 2). In Patent Documents 1 and 2, the influence of fluorescence is removed by calculation from spectra observed in the Raman spectroscopy, thereby achieving that Raman spectra can be obtained with higher signal-to-noise ratio.

However, the method of Patent Document 1 needs to obtain two or more spectra, resulting in longer measurement time than conventional methods. In addition, when a sample may make a change by irradiating light, two or more measurements result in loss of information other than fluorescence. The method of Patent Document 2 makes a change of wavelength similarly to the method of Patent Document 1, resulting in longer measurement time than conventional methods. In addition, the method of Patent Document 2 uses incoherent light, so that the band of irradiating light is broadened, resulting in deterioration of wavenumber resolution.

Furthermore, the methods of Patent Documents 1 and 2 cannot substantially achieve the separation of a fluorescence spectrum and a Raman spectrum. For this reason, when the intensity of a fluorescence spectrum is higher than the intensity of a Raman spectrum and beyond the dynamic range of a detector, their separation cannot become achieved.

Fluorescence emission occurs because excited electrons release their energies in the transition. In addition, fluorescence emission has a broad spectrum depending on how the vibration states of molecules are occupied. Stimulated emission is a phenomenon that excited electrons release energy in the transition having the same phase and frequency as those of light introduced from the outside. The molecules after introduction of relaxation light have lost their energies, thereby failing to emit fluorescence.

For example, a confocal microscope with high spatial resolution has been developed by introducing relaxation light into the microscopic observation (Non-Patent Document 1). In Non-Patent Document 1, fluorescence in any other portion than the central portion to be observed is removed by introducing relaxation light into the confocal fluorescence microscope to obtain a fluorescence signal only from the central portion, so that the confocal fluorescence microscope may have improved spatial resolution. The introduction of relaxation light keeps fluorescence emission efficiency low.

Patent Document 3 discloses a method of suppressing fluorescence by stimulated emission. In Examples of Patent Document 3, a pulse laser having a pulse width of 10 picoseconds or smaller is used as a pump light source for inducing a Raman process. However, the line width of pump light is important in the Raman scattering observation as a linear optical process. For example, pulse widths of 10 picoseconds or smaller may make spectral widths broadened by uncertainty principle, so that, high wavenumber resolution cannot be obtained to provide an effective measurement.

The present invention has been made in view of the above-described problems, and an object of the present invention is to provide a Raman microscope and a Raman spectrometric measuring method, in which a spectrometric measurement can be made with high wavenumber resolution.

The Raman microscope of the present invention comprises: a pump light source for emitting pump light as continuous light; a relaxation light source for emitting relaxation light to induce stimulated emission in a sample; an optical system for irradiating the relaxation light and the pump light to the sample; and a detector for detecting Raman scattered light generated in the sample. The use of continuous light for the pump light makes it possible to narrow the line width of the pump light, so that the measurement of Raman scattered light can be made with high wavenumber resolution.

In the Raman microscope, an embodiment may preferably be carried out, in which the wavelength of the relaxation light is within 4000 cm$^{-1}$ on the long-wavelength side from the wavelength of the pump light. This is because the generation of fluorescence may be even more suppressed in some cases.

In the Raman microscope, a spectrograph may preferably be provided, which separates Raman scattered light from light generated in the sample. The separation of Raman scattered light by a spectrograph makes it possible to measure Raman scattered light with even higher SN ratio.

In the Raman microscope, the relaxation light may be continuous light. This makes it possible to suppress the generation of fluorescence effectively in the sample.

In the Raman microscope, it may preferably comprise an optical modulator for strength modulating the relaxation light or the pump light to make the filtering of a fluorescence component or components contained in the signal from the detector. This allows the effective removal of a fluorescence component or components contained in the signal from the detector.

In the Raman microscope, the relaxation light and the pump light may preferably be irradiated to the sample through a single-mode fiber. This makes it possible to make a stable measurement.

The Raman microscope may preferably further comprise a first fiber cable for introducing the pump light; a second fiber cable for introducing the relaxation light; and a fiber combiner for combining the first fiber cable and the second fiber cable. This makes it possible to make an effective measurement of Raman scattered light.

In the Raman microscope, the relaxation light may preferably enter the sample through a dark-field irradiation optical system. This makes it possible to prevent the relaxation light from the relaxation light source from entering the spectrograph.

The Raman microscope may preferably further comprise at least one of a phase plate into which the pump light is introduced or a phase plate into which the relaxation light is introduced.

The Raman spectrometric measuring method of the present invention comprises the steps of emitting pump light as continuous light; emitting relaxation light to induce stimulated emission in a sample; irradiating the relaxation light and the pump light to the sample; and detecting Raman scattered light generated in the sample. The use of continuous light for the pump light, makes it possible to narrow the line width of the pump light, so that the measurement of Raman scattered light can be made with high wavenumber resolution.

In the Raman spectrometric measuring method, an embodiment may preferably be carried out, in which the wavelength of the relaxation light is within 4000 cm$^{-1}$ on the long-wavelength side from the wavelength of the pump light. This is because the generation of fluorescence may be even more suppressed in some cases.

The Raman spectrometric measuring method may preferably further comprise the step of spectrally separating Raman scattered light from light generated in the sample. The spectral separation of Raman scattered light makes it possible to measure Raman scattered light with even higher SN ratio.

In the Raman spectrometric measuring method, the relaxation light may be continuous light. This makes it possible to suppress the generation of fluorescence.

In the Raman spectrometric measuring method, the relaxation light or the pump light may preferably be intensity-modulated to remove fluorescence components with a filter, which components are contained in a signal obtained in the above detecting step. The fluorescence components contained in a signal from a detector can effectively be removed.

In the Raman spectrometric measuring method, an embodiment may be employed, in which the wavelength of the relaxation light is changed to detect a spectrum; the wavelength of the relaxation light is selected according to the spectrum detected above; and the relaxation light having the wavelength selected above is irradiated to the sample to detect Raman scattered light in another portion. This makes it possible to improve the signal-to-noise ratio of Raman scattered light.

In the Raman spectrometric measuring method, an embodiment may be employed, in which the intensity of the relaxation light is changed to detect a spectrum: the intensity of the relaxation light is selected according to the spectrum detected above; and the relaxation light having the intensity selected above is irradiated to the sample to detect Raman scattered light in another portion. This makes it possible to improve the signal-to-noise ratio of Raman scattered light.

In the Raman spectrometric measuring method, an embodiment may preferably be employed, in which the relaxation light and the pump light are irradiated to the sample through a single-mode fiber. This makes it possible to make a stable measurement.

In the Raman spectrometric measuring method, the direction of polarization in the relaxation light and the direction of polarization in the pump light may preferably be made orthogonal or parallel with each other in the sample. This makes it possible to suppress the generation of stimulated Raman scattered light, so that the signal-to-noise ratio of Raman scattered light can be improved.

According to the present invention, there can be provided a Raman microscope and a Raman spectrometric measuring method, in which a measurement can be made with high wavenumber resolution.

DETAILED DESCRIPTION OF THE INVENTION

In an embodiment of the present invention, when Raman spectroscopic observation is carried out, pump light exciting spontaneous Stokes Raman scattering (in the following description, Raman scattered light means spontaneous Stokes Raman scattering generated on the long-wavelength side as compared with irradiating light by a linear optical process) is irradiated to a sample through an objective lens. At this time, relaxation light exciting stimulated emission is coaxially introduced into the same optical route as that of the pump light. The introduction of the relaxation light makes it possible to suppress broadband fluorescence emission coming to be mixed in Raman spectra. The sample in an excited state emits monochroic light by stimulated emission and returns to the ground state. This makes it possible to suppress fluorescence emission even in a sample emitting fluorescence that may overlap the Raman scattering spectrum. Therefore, a measurement with high signal-to-noise ratio can be achieved. Furthermore, the use of continuous light makes it possible to achieve observation with high wavenumber resolution.

The following will describe some embodiments to which the present application can be applied. The following description is intended to describe some embodiments of the present invention, but is not intended to limit the present invention to the following embodiments. For its clarification, the following description may include appropriate abbreviations and simplification. In addition, the respective elements in the following embodiments can easily be modified, added, and/or changed within the scope of the present invention, if by a person of ordinary skill in the art. In the respective drawings, the same reference numerals indicate the same elements, of which descriptions may appropriately be abbreviated.

The present application claims the benefit of priority based on Japanese Patent Application No. 2011-127217 filed on Jun. 7, 2011. The disclosure of Japanese Patent Application No. 2011-127217 filed on Jun. 7, 2011 is incorporated herein by reference in its entirety.

Embodiment 1

Figure 2:
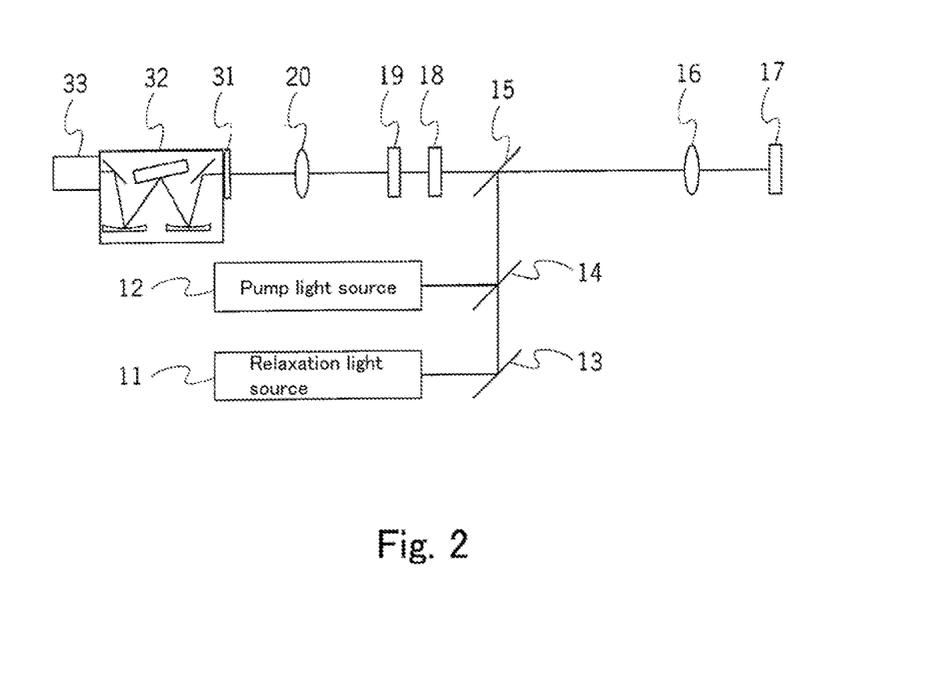
FIG. 2 is a diagram showing the optical system of a Raman microscope according to Embodiment 1.

The Raman microscope and Raman spectrometric measuring method according to Embodiment 1 will be described with FIG. 2. FIG. 2 is a diagram showing the entire structure of an optical system of the Raman microscope. A relaxation light source 11 is, for example, a continuous wave laser light source, and it emits light generating stimulated emission (such light is hereinafter referred to as relaxation light) in a sample 17. The relaxation light from the relaxation light source 11 is reflected on a mirror 13 and enters a dichroic mirror 14. A pump light source 12 is a continuous wave laser light source and emits monochroic pump light. The pump light from the pump light source 12 enters the dichroic mirror 14. The dichroic mirror 14 transmits or reflects light depending on its wavelength. More specifically, the dichroic mirror 14 transmits the relaxation light and reflects the pump light. Therefore, combined light is generated by the dichroic mirror 14, which light was obtained, by the combination of the pump light and the relaxation light. The pump light and the relaxation light, which were combined, by the dichroic mirror 14, coaxially propagate and enter a dichroic mirror 15. The combined light of the pump light and the relaxation light is reflected by the dichroic mirror 15, followed by being collected by an objective lens 16 and entering the sample 17.

Raman scattered light generated in the sample 17 enters the dichroic mirror 15 through the objective lens 16. The dichroic mirror 15 transmits the Raman scattered light and reflects the pump light and the relaxation light. Therefore, the Raman scattered light is separated from the pump light and the relaxation light by the dichroic mirror 15. Furthermore, notch filters 18 and 19 limiting the transmission of light depending on its wavelength are disposed downstream of the dichroic mirror 15. The notch filter 18 limits the transmission of the relaxation light, and the notch filter 19 limits the transmission of the pump light. The relaxation light and the pump light, both entering a spectrograph 32, can further be reduced by the notch filter 18 and the notch filter 19. The Raman scattered light from the dichroic mirror 15 enters a lens 20 through the notch filer 18 and the notch filter 19.

The lens 20 collects the Raman scattered light on a spatial filter 31. The spatial filter 31 is a slit, a pinhole, or the like. The Raman scattered light passed through the spatial filter 31 enters the spectrograph 32. The spectrograph 32 comprises a dispersive element such as a grating or a prism, in which the Raman scattered light entered from the spatial filter 31 is spatially dispersed depending on its wavelength. When the spatial filter 31 has a slit, the spectrograph 32 disperses the Raman scattered light in a direction perpendicular to the slit. The Raman scattered light spectrally separated by the spectrograph 32 enters a detector 33. The detector 33 is a line sensor having linearly arranged light-receiving elements or an area sensor having matrically arranged light-receiving elements. More specifically, the detector 33 is a two-dimensional array photodetector such as a two-dimensional CCD camera having arranged pixels. This makes it possible to detect the wavelength dispersed Raman scattered light with one flame of the detector 33.

In Patent Document 3 described above, a photomultiplier is used as the photodetector, but it cannot simultaneously measure light of many wavelengths, thereby requiring much time to obtain a spectrum. For this reason, the method of Patent Document 3 cannot make high-speed Raman spectroscopic imaging. However, as shown in this Embodiment, light of two or more wavelengths can be detected by one-frame imaging using an imaging spectrometer as the detector 33, in which spectrometer light-receiving elements are arranged in a direction perpendicular to the direction of wavelength dispersion by the spectrograph 32. This makes it possible to shorten measurement time.

In the Raman microscope shown in FIG. 2, the pump light source 12 as a point light source is disposed in a position conjugate to the sample 17. In addition, the spatial filter 31 is disposed in a position conjugate to the sample 17. The spatial filter 31 is used as a pinhole or a slit in the confocal optical system, and the Raman microscope forms a confocal microscope. Spatial resolution can be improved by detecting the Raman scattered light through the confocal optical system. When a slit is used as the spatial filter 31, light from the pump light source 12 and the relaxation light source 11 is one-dimensionally scanned at a higher rate than the imaging rate of the detector 33, or converted into line-shaped light beam. This makes it possible to form a line confocal (a slit confocal optical system).

In addition, the Raman scattered light at an arbitrary position of the sample 17 can be spectrometrically measured by relatively moving the position of the pump light and the relaxation light at the sample 17 with a scanner deflecting the pump light and the relaxation light, a movable stage for placing the sample 17, or the like. The Raman spectrum in the entire or prescribed region of the sample 17 is observed by scanning the sample 17.

The beam diameters of the pump light and the relaxation light may more preferably be made substantially the same. This is because fluorescence can be suppressed in a wider region containing the defocusing position of the sample when the overlapping portion of the pump light and the relaxation light is wider. The beam diameter can be adjusted by providing a beam expander (not shown) of appropriate power just after each or one of the light sources.

Furthermore, in this Embodiment, a light source capable of emitting continuous light is used as the pump light source in contrast to the method of Patent Document 3. Therefore, the following effects can be attained.

(1) Continuous light can always put molecules into an excited state, and the molecules can be saturated into the excited state. At this time, when relaxation light is introduced, it is not absorbed, but all parts of the light induce the stimulated emission effect. When Raman scattering is observed with continuous wave light, the pump light has enough intensity ($>10^5$ W/cm$^2$) to cause the excitation saturation of the molecules, relative to the average intensity (about $10^4$ W/cm$^2$) of pulse light. For this reason, the molecules can cause excitation saturation and effective stimulated emission, so that fluorescence-to-Raman ratio is reduced, thereby improving signal-to-noise ratio.

(2) When Raman scattered light of the same intensity is tried to be obtained (when each light source has the same average intensity), pulse laser is liable to damage a sample because of its having high peak intensity. In the case of continuous light, it hardly damages a sample even when it has increased average intensity, so that intensive Raman scattering can be obtained with an increase in the intensity of light source, thereby improving signal-to-noise ratio.

(3) When pulse laser is used, optical components having high damage threshold should be used because the pulse laser has high peak intensity. For this reason, usable optical components are limited. When continuous wave laser is used, limitation by damage threshold value is small, so that higher performance optical parts can be used (such as filters having higher transmittance of Raman scattered light).

(4) The use of pulse laser may possibly cause light emission due to undesired non-linear optical effects such as multiphoton excitation, harmonic generation, and photoparametric oscillation, resulting in the possible inhibition of measurement. However, there is no such problem in the case of continuous light.

(5) In the case of pulse laser, there is time between two pulses, which involves no generation of Raman scattered light. In this time, it results in the accumulation of only dark current in the detector to reduce signal-to-noise ratio. There is no such problem in the case of continuous light.

(6) In the case of continuous light, fluorescence emission may further be suppressed in some cases depending on a sample by further making the electronic excited triplet state into the superexcited state.

(7) When continuous wave laser is irradiated, discoloration may easily occur as compared with the case of pulse laser, and the effect of reducing fluorescence intensity can be attained even by such discoloration.

(8) When pump light and relaxation light are both pulsed light, the respective laser pulse periods should be made coincident with each other to cause effective stimulated emission, and furthermore, timing should be adjusted in such a manner that relaxation light enters a sample about several picoseconds late. The use of continuous light for each makes such adjustment unnecessary, resulting in simplification of apparatus design. There is no possibility of performance degradation caused by deviation (jitter) of pulse period or shifting of timing adjustment.

(9) Continuous wave laser can be made to have a narrower (monochromatic) spectrum as compared with pulse laser. The use of narrower spectrum laser improves the wavenumber resolution of a Raman spectrum obtained.

(10) The use of narrow spectrum laser prevents lenses from causing chromatic aberration, thereby making unnecessary correction of chromatic aberration in the irradiating optical system (up to the dichroic mirror 15). In addition, there is no deterioration of spatial resolution by chromatic aberration, thereby making it possible to achieve high spatial resolution.

(11) In general, continuous wave laser has high intensity stability as compared with pulse laser. In addition, continuous wave laser requires short rise time, thereby making it possible to use an apparatus in a short warm-up period.

(12) In the wavelength region used for Raman spectroscopy, continuous wave laser may be inexpensive in many cases.

As the pump light source 12, it is preferable to use monochromatic laser light, particularly laser light having a line width of 1 cm$^{-1}$ or smaller. This makes it possible to obtain a Raman spectrum with high wavenumber resolution. It is also preferable to use a laser operated in TEM00 mode to achieve high spatial resolution as a microscope and having an M2 factor of two or lower. As such a laser, there can be used Torus available from Laser Quantum Ltd.

For the relaxation light source 11, it is preferable to use a light source having intensity equal to or higher than that of the pump light. In addition, the relaxation light to be used may have the center wavelength greater than the center wavelength of the pump light. More preferably, the relaxation light may be adjusted to be greater by 4000 cm$^{-1}$ or more than the center wavelength of the pump light. This is because the relaxation light does not overlap with a region from 0 cm$^{-1}$ to 4000 cm$^{-1}$, in which Raman scattered light is ordinarily measured. For example, when pump light of 488 nm in wavelength is used, the region from 0 cm$^{-1}$ to 4000 cm$^{-1}$ corresponds to the region from 488 nm to 606 nm, and therefore, adjusting the center wavelength of relaxation light to 606 nm or greater makes it possible that the Raman scattered light and the relaxation light do not overlap with each other. As such a light source, there can be used Ignis available from Laser Quantum Ltd. oscillating at 671 nm.

In contrast, the present inventors have found that it is also useful to use light within 4000 cm$^{-1}$ in wavelength from pump light for relaxation light. In particular, when fluorescence can effectively be suppressed by relaxation light within 4000 cm$^{-1}$ in wavelength, relaxation light within 4000 cm$^{-1}$ in wavelength may preferably be used. In this case, the measurement of Raman scattered light is difficult in the wavelength region near relaxation light because the Raman scattered light is inhibited by the relaxation light. When Raman scattered light only in part of the wavelength region is of interest, there can be used relaxation light outside this interested wavelength region. To make narrow the wavelength region in which the measurement is inhibited, it is preferable to use narrow spectrum relaxation light of 100 cm$^{-1}$ or smaller in line width. A wavelength involving the effective suppression of fluorescence is a wavelength involving the intensive generation of fluorescence. Therefore, in the situation that intensive fluorescence is generated in the region within 4000 cm$^{-1}$ from pump light to inhibit the measurement of Raman scattered light, it is particularly effective to use relaxation light within 4000 cm$^{-1}$ in wavelength. Furthermore, the wavelength of relaxation light, can be adjusted within 3000 cm$^{-1}$ or 2000 cm$^{-1}$ from pump light.

The relaxation light source 11 may preferably be selected from light sources having variable emission wavelengths and having such a structure that the center wavelength can be optimized to a wavelength involving the most effective suppression of fluorescence. As the relaxation light source 11, for example, a wavelength variable and continuous wave titan-sapphire laser can be used. Alternatively, the wavelength of part of broad wavelength spectrum light source may be selected with a bandpass filter. In addition, the use of the continuous wave relaxation light source 11 makes it possible to suppress the generation of fluorescence more effectively.

The wavelength of relaxation light can be optimized by the following procedures.

1. A spectrum between the wavelength of pump light, and the wavelength of relaxation light is measured while gradually changing the wavelength of relaxation light.

2. In the spectrum measured in item 1, the wavelength of relaxation light is regarded as the optimized wavelength when the ratio of the peak intensity of a Raman scattered spectrum and the background intensity of fluorescence becomes highest.

In this way, the wavelength of relaxation light is optimized at one or several, portions of the sample 17. Then, using relaxation light having the optimized wavelength thus selected, the entire or prescribed region of the sample 17 is observed. This makes it possible to achieve observation with high signal-to-noise ratio.

Similarly, it is also preferable to optimize the intensity of relaxation light. The intensity of relaxation light is regarded as the optimized intensity when the ratio of the peak intensity of a Raman scattered spectrum and the background intensity of fluorescence becomes highest in the measurement while gradually changing the intensity of relaxation light. The intensity of relaxation light is optimized at one or several portions of the sample 17. Then, making relaxation light have the optimized intensity, the entire or prescribed region of the sample 17 is observed. This makes it possible to achieve observation with high signal-to-noise ratio. Furthermore, to obtain the maximum effect of stimulated emission, it is preferable to optimize both the beam diameters of pump light and relaxation light, which enter an objective lens, so that the ratio of wavelength and numerical aperture becomes equal.

The relaxation light source may have a wide spectrum (not monochromatic), so long as relaxation light does not overlap with the region of Raman scattered light, and therefore, light source other than laser light source can be used.

The dichroic mirror 15 reflecting two light beams may have a structure that has a coating on both sides and reflects pump light on one side and relaxation light on the other side. The use of such a dichroic mirror makes it possible to make easy the design of coating.

For the detection of Raman scattered light, it is not always necessary to use a spectrograph, but an optical filter may also be used alternatively, which transmits Raman scattered light having a prescribed wavelength.

Embodiment 2

Figure 3:
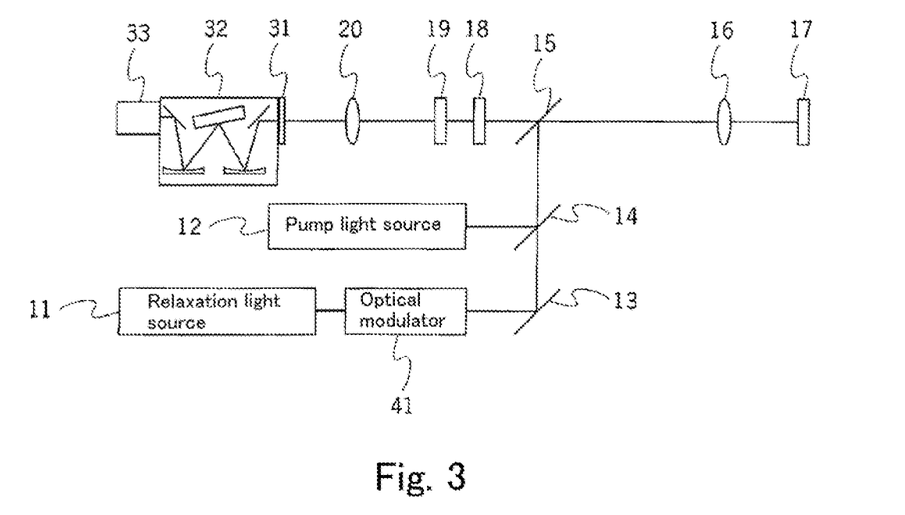
FIG. 3 is a diagram showing the optical system of a Raman microscope according to Embodiment 2.

The Raman microscope and Raman spectrometric measuring method according to Embodiment 2 will be described with FIG. 3. FIG. 3 is a diagram showing the entire structure of the Raman microscope. In this Embodiment, an optical modulator 41 is disposed between the relaxation light source 11 and the mirror 13. The optical modulator 41 causes the temporal intensity modulation of relaxation light. In addition, as the detector 33, a line detector is used, in which photomultipliers or avalanche photodiodes faster than CCDs are arranged in one line. In this regard, the other structure is the same as that of Embodiment 1, except the optical modulator 41 and the detector 33, and therefore, its description is omitted.

The relaxation light from the relaxation light source 11 is released from the optical modulator 41 to enter the mirror 13. The optical modulator 41 causes intensity modulation, for example, in such a manner that the optical intensity of relaxation light is proportional to $(1+\cos\omega t)$. The relaxation light reflected on the mirror 13 enters a dichroic mirror 14. In addition, pump light from a pump light source 12 also enters the dichroic mirror 14. Then, similarly to Embodiment 1, combined light of the pump light and the relaxation light by the dichroic mirror 14 enter the sample 17. Raman scattered light generated in the sample 17 is detected with the detector 33, similarly to Embodiment 1.

To a signal from the detector 33, a frequency low-pass filter is applied, which transmits a signal having a lower frequency than the modulation frequency, thereby making it possible to obtain a signal having reduced fluorescence. More specifically, the use of a frequency low-pass filter transmitting a signal having a lower frequency than the modulation frequency of the optical modulator removes fluorescence components to obtain the signal of Raman scattering. Alternatively, the difference is taken by the intensity of relaxation light, thereby making it possible to obtain only the fluorescence signal and subtract the fluorescence signal from the spectrum obtained. In this way, the relaxation light is intensity modulated, and the signal from the detector 33 is subjected to the electrical removal of high-frequency components. This makes it possible to remove fluorescence components effectively, thereby achieving a spectrometric measurement with high signal-to-noise ratio.

Modified Example

Figure 4:
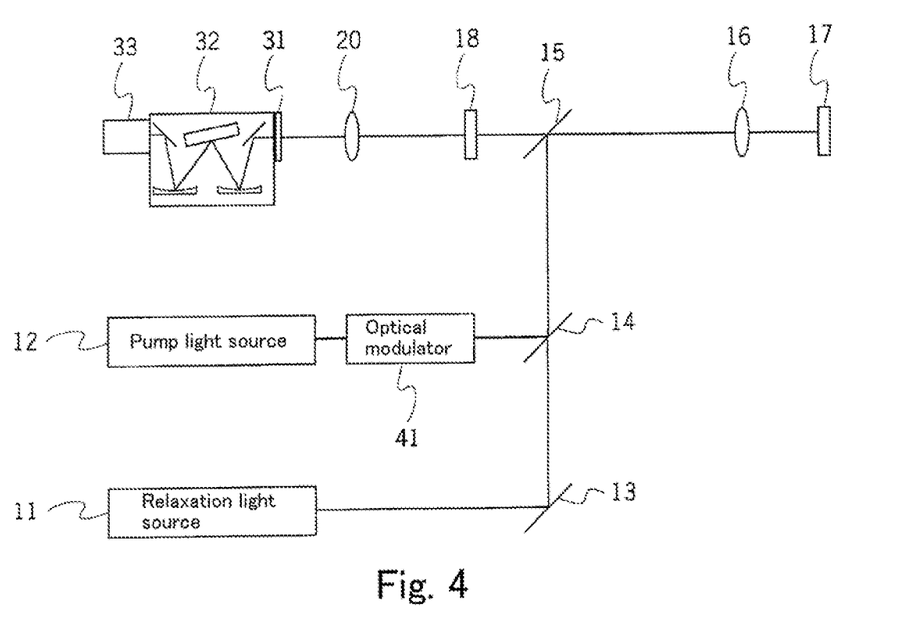
FIG. 4 is a diagram showing the optical system of a Raman microscope according to a modified example of Embodiment 2.

In a Modified Example of Embodiment 2, relaxation light is not modulated, but pump light is modulated. Therefore, as shown in FIG. 4, the optical modulator 41 is disposed between the pump light source 12 and the dichroic mirror 14. The pump light modulated in the optical modulator 41 is combined with the relaxation light in the dichroic mirror 14. The pump light is optically modulated, and a frequency high-pass filter is used in the detector 33. When the optical modulator 41 modulates the pump light at a frequency not following the response frequency (several nanoseconds) of fluorescence, the response of fluorescence cannot follow, but the response (several picoseconds) of Raman scattering can follow. For this reason, the signal of Raman scattering can be obtained by lock-in detection in the modulation frequency. This makes it possible to remove fluorescence components effectively, thereby achieving a spectrometric measurement with high signal-to-noise ratio.

In this way, fluorescence components contained in the signal of the detector 33 can be removed by the use of the filter together with the placement of the optical modulator 41 in FIGS. 3 and 4. This makes it possible to measure the spectrum of Raman scattered light with higher signal-to-noise ratio. In this regard, the term "filter" as used herein is not limited to an electrical filter, but filtering may also be carried out by arithmetic processing of digital detected data. More specifically, not only an electrical filter, but also filtering software, may be used, so long as it is a method capable of filtering fluorescence components contained in the signal of the detector 33. In this case, the signal of the detector 33 is converted into digital data, which is incorporated into the arithmetic processing unit of a PC (personal computer) or the like. Then, a prescribed program is run in the arithmetic processing unit to achieve filtering.

Embodiment 3

Figure 1:
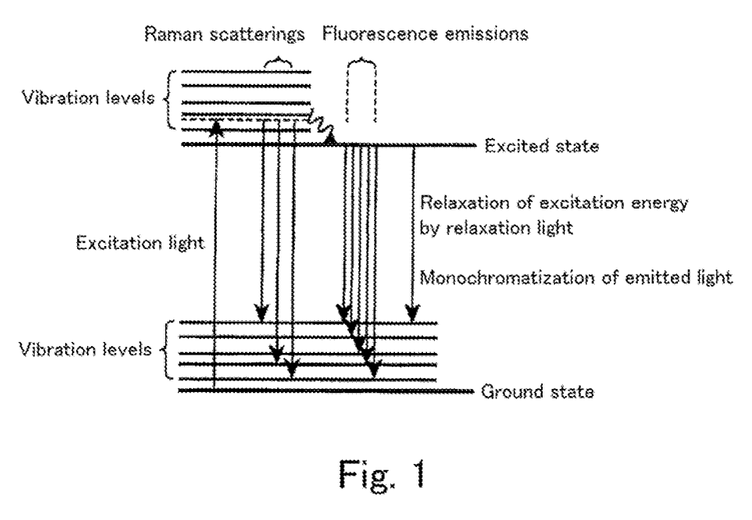
FIG. 1 is a diagram showing the induction of excitation energy by simulated emission.

Embodiment 3 is different in the position of combining relaxation light and pump light from Embodiments 1 and 2. The basic structure except this difference is the same as that of Embodiment 1, and therefore, its description is omitted. The structure of the Raman microscope according to Embodiment 3 will be described with FIG. 5. In this Embodiment, a dichroic mirror 44 is used in place of the dichroic mirror 14 to combine pump light and relaxation light. More specifically, the dichroic mirror 14 is removed from the structure shown in FIG. 1, and the dichroic mirror 44 is disposed between the dichroic mirror 15 and the objective lens 16. The relaxation light from the relaxation light source 11 directly enters the dichroic mirror 44. The pump light from the pump light source 12 enters the dichroic mirror 15 through the mirror 43.

The pump light reflected on the dichroic mirror 15 enters the dichroic mirror 44 through the notch filter 18. The dichroic mirror 44 reflects the relaxation light and transmits the pump light. Therefore, the dichroic mirror 44 produces combined light by combining the pump light and the relaxation light. This results in that the relaxation light and the pump light coaxially propagate and enter the objective lens 16, similarly to Embodiment 1. In the case of the structure shown in FIG. 5, the notch filter 18 removing the relaxation light is disposed between the dichroic mirror 15 and the dichroic mirror 44, but the position of the notch filter 18 is not particularly limited, so long as it is between the dichroic mirror 44 and the spatial filter 31.

Figure 5:
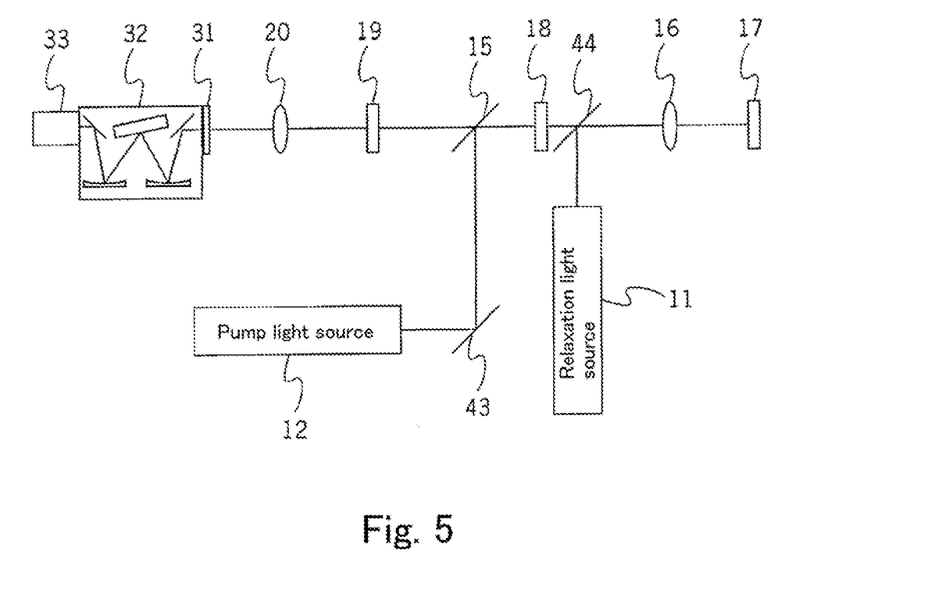
FIG. 5 is a diagram showing the optical system of a Raman microscope according to Embodiment 3.

In this way, the relaxation light and the pump light may be superimposed anywhere, so long as it is in the pathway before irradiating the sample 17. In this optical system, the relaxation light can improve signal-to-noise ratio, regardless of the optical system on or after the dichroic mirror 44.

Embodiment 4

Figure 6:
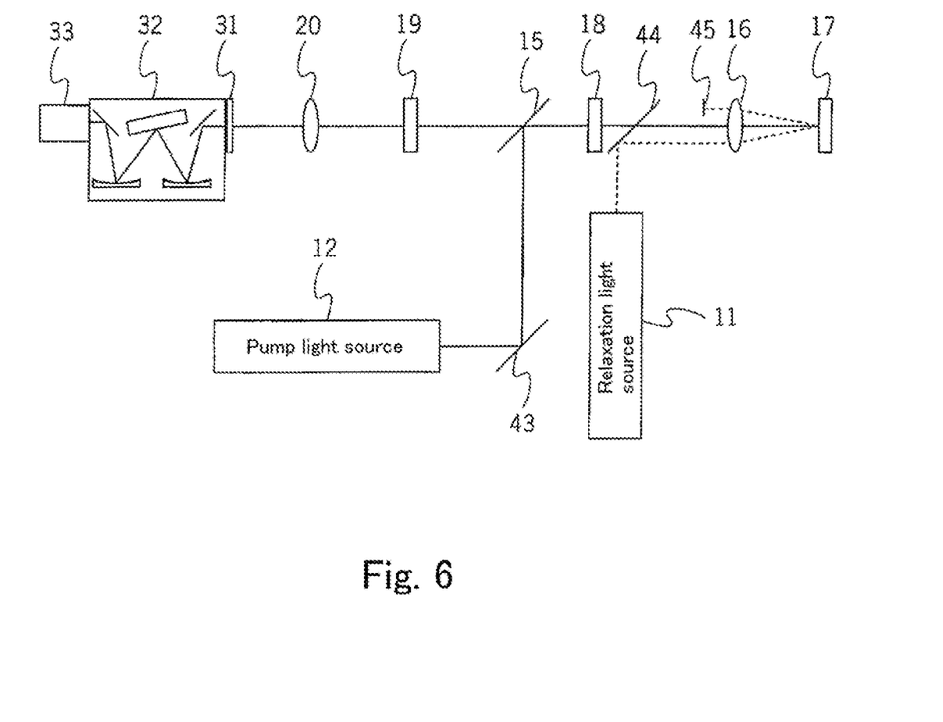
FIG. 6 is a diagram showing the optical system of a Raman microscope according to Embodiment 4.

In Embodiment 4, the relaxation light is irradiated to the sample 17 by a dark-field irradiation optical system as shown in FIG. 6. The basic structure is the same as that of Embodiments 1 and 3, except this difference, and therefore, its description is omitted. In this Embodiment, the entering position of the relaxation light in the dichroic mirror 44 is deviated from the optical axis of the pump light. Therefore, the propagating direction (optical axis) of the relaxation light is slightly slanted, from the propagating direction (optical axis) of the pump light between the objective lens 16 and the sample 17, and therefore, the relaxation light enters on a slant with respect to the sample 17. The pump light and the relaxation, light, which were refracted by the objective lens 16, are spatially superimposed on the sample 17. The pump light and the relaxation light, which were spatially superimposed, can be irradiated to the sample 17. Then, the relaxation light reflected on the sample 17 is blocked by a light stopper 45 disposed between the objective lens 16 and the dichroic mirror 44. As can be seen from the above, in this Embodiment, the relaxation light is irradiated to the sample 17 by dark-field irradiation, and therefore, the relaxation light can be prevented from entering the spectrograph 32. Accordingly, observation with higher signal-to-noise ratio can be achieved.

Embodiment 5

Figure 7:
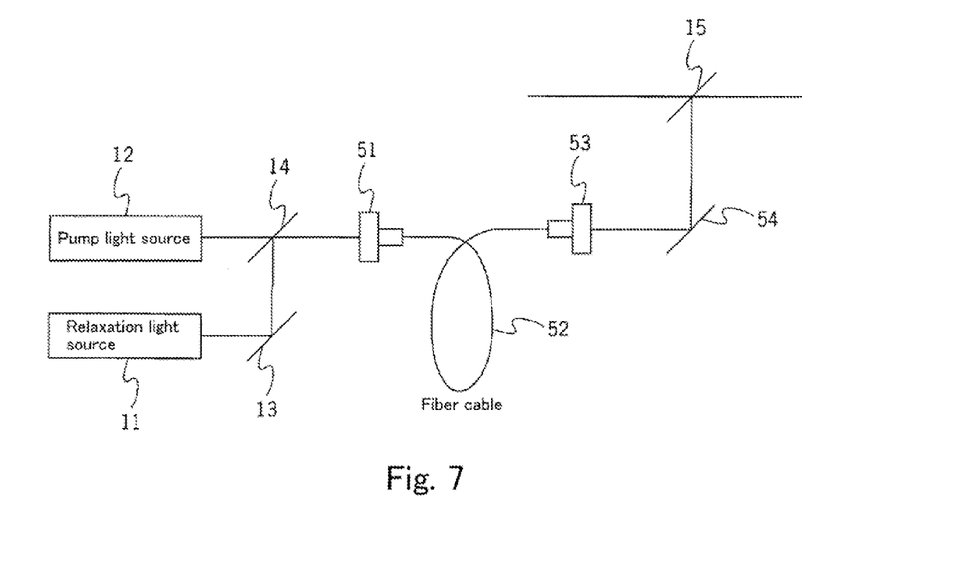
FIG. 7 is a diagram showing the optical system of a Raman microscope according to Embodiment 5.

In Embodiment 1, it is preferable to use a single-mode fiber for the introduction of the pump light and the relaxation light. For this reason, in this Embodiment, as shown in FIG. 7, a single-mode fiber cable 52, a fiber coupler 51, and a fiber coupler 53 are disposed in the light path on the way to the sample 17. The basic structure of the Raman microscope is the same as that of Embodiment 1, and therefore, its description is omitted. FIG. 7 is shown by omission about the structure ranging from the dichroic mirror 15 to the sample 17, and the structure ranging from the dichroic mirror 15 to the detector 33.

The pump light and the relaxation light, which were combined by the dichroic mirror 14, enter a fiber coupler 51. The fiber coupler 51 is connected to one end of a fiber cable 52. The other end of the fiber cable 52 is connected to a fiber coupler 53. The pump light and the relaxation light, which entered the fiber coupler 51, propagate in the single-mode fiber cable 52 and exit out the fiber coupler 53. The pump light and the relaxation light, which exited out the fiber coupler 53, enter the dichroic mirror 15 through a mirror 54.

Such a structure surely makes it possible to introduce the pump light and the relaxation light coaxially into the optical system. In addition, the pump light source and the relaxation light source as the main heat generation sources in the apparatus can be disposed away from the other components of the apparatus, so that the deviation of the optical system can be prevented from occurring by the heat generation of the light sources. As a result, light beams from two light sources can be kept coaxially over a long period after adjusting the optical system.

In addition, the use of a single-mode fiber makes it possible to align the beam diameters of pump light and relaxation light without using an adjusting means such as a beam expander. When the beam diameters of pump light and relaxation light are aligned, the overlapping portion between the pump light and the relaxation light becomes increased, and therefore, fluorescence can be suppressed in a wide region containing the defocusing position of a sample.

Modified Example

Figure 8:
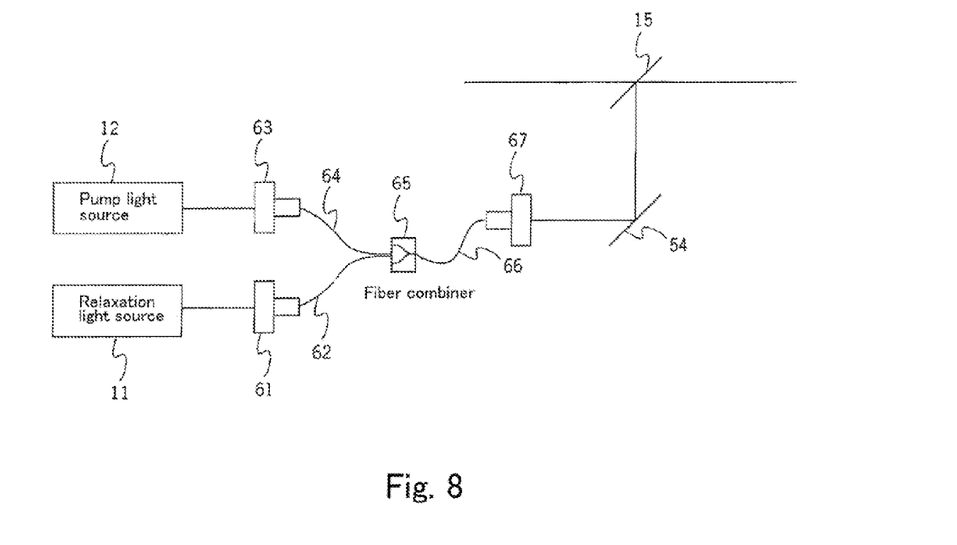
FIG. 8 is a diagram showing the optical system of a Raman spectrophotometer according to a modified example of Embodiment 5.

Furthermore, as shown in FIG. 8, the pump light and the relaxation light may preferably be superimposed by a fiber combiner 65. In this case, the mirror 13 and the dichroic mirror 14 become unnecessary. The fiber combiner 65 has a structure such that two or more optical fibers are stretched and joined together while being fused by heat, and light leaking from the core is split or combined between the optical fibers.

As shown in FIG. 8, relaxation light from the relaxation light source 11 enters a fiber coupler 61, and pump light from the pump light source 12 enters a fiber coupler 63. The relaxation light entered the fiber coupler 61 propagates in a fiber cable 62 and enters the fiber combiner 65. The pump light entered the fiber coupler 63 propagates in a fiber cable 64 and enters the fiber combiner 65. The fiber combiner 65 combines the fiber cable 64 and the fiber cable 62, and therefore, the pump light and the relaxation light are combined by the fiber combiner 65. The pump light and the relaxation light combined by the fiber combiner 65 propagate in a fiber cable 66 and emits out a fiber coupler 67. The combined light, which was emitted from the fiber coupler 67, is reflected by the mirror 54 to enter into the dichroic mirror 15.

Such a structure makes it possible to prevent the efficiency of coupling into a fiber from being lowered by a change in mirror angle over time. Furthermore, the use of a single-mode fiber makes it possible to obtain the same effect as shown in FIG. 7.

Embodiment 6

Figure 9:
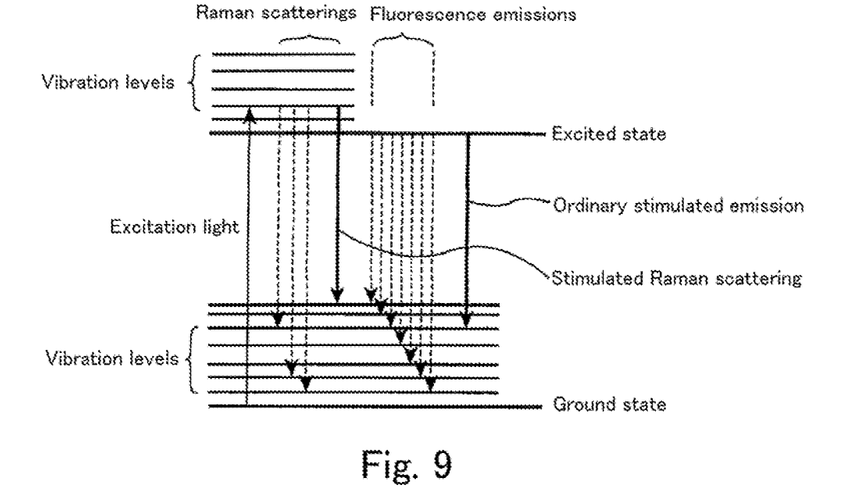
FIG. 9 is a Jablonski diagram showing the generation of stimulated Raman scattering.

Depending on the type of sample to be measured, stimulated Raman scattering may occur in some cases by the irradiation of relaxation light, resulting in a reduction of Raman scattered light, as shown in the Jablonski diagram of FIG. 9. The generation efficiency of stimulated Raman scattering depends on the wavelength of relaxation light, and therefore, the S/N ratio of Raman spectra can be improved by appropriately selecting the wavelength of relaxation light, also taking into consideration the efficiency of stimulated Raman scattering. Therefore, when a sample involving the generation of stimulated Raman scattering is used, contrary to the cases described in Embodiments 1 to 5, the selection of a wavelength involving the most effective suppression of fluorescence as the central wavelength of relaxation light does not mean the selection of an optimum wavelength for measuring Raman spectra with a high S/N ratio.

The generation of stimulated Raman scattering can be reduced by appropriately setting the polarization direction of pump light and relaxation light entering into a sample. The polarization direction of reducing stimulated Raman scattering depends on the type of sample and the wavelengths of pump light and relaxation light.

In many cases, the generation efficiency of stimulated Raman scattering can be lowered by making the polarization direction of pump light and the polarization direction of relaxation light orthogonal or parallel to each other in a sample. In this regard, the polarization direction in a sample cannot be confirmed directly, but it is only necessary in ordinary cases to confirm the polarization direction of light, entering into an objective lens.

Figure 10:
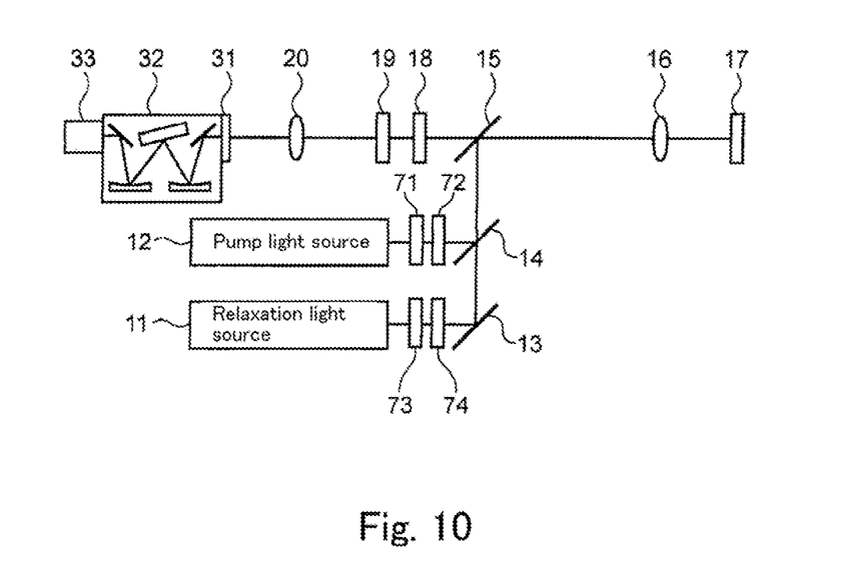
FIG. 10 is a diagram showing the optical system of a Raman microscope according to Embodiment 6.

FIG. 10 shows the optical system of the Raman microscope according to Embodiment 6. The optical system of the Raman microscope according to Embodiment 6 is substantially the same as the optical system of the Raman microscope according to Embodiment 1, but it is different from that of Embodiment 1 in that it has a structure capable of adjusting the polarization state of light emitted from the pump light source 12 or the relaxation light source 11.

In FIG. 10, a $\lambda/2$ plate 72 and a $\lambda/4$ plate 71 are disposed between the pump light source 12 emitting linear polarized light and the dichroic mirror 13. In addition, a $\lambda/2$ plate 74 and a $\lambda/4$ plate 73 are disposed between the relaxation light source 11 emitting linear polarized light and the mirror 13. The polarization states of pump light and relaxation light in a sample can be set by adjusting the angles of these $\lambda/2$ plates 72, 74 and $\lambda/4$ plates 71, 73. The use of these four wave plates makes it possible to convert the pump light and the relaxation light to linear polarized light in the sample, while correcting the influence of optical components between the light sources and the sample.

When the influence of optical components between the light sources and the sample is small, the polarization states can be set by using only a $\lambda/2$ plate. Alternatively, when the wavelengths and polarization states of pump light and relaxation light, relative to a sample, have already been optimized, and therefore, the influence of optical components between the light sources and the sample is small, $\lambda/2$ plates and $\lambda/4$ plates can be omitted by selecting the polarization states of optical sources themselves.

Even in the optical systems of not only the Raman microscope according to Embodiment 1, but also the Raman microscopes according to Embodiments 2 to 4, the polarization states in a sample can be set by disposing $\lambda/2$ plates and $\lambda/4$ plates between the light sources and the position of superimposing pump light and relaxation light.

Besides, in the optical system of the Raman microscope according to Embodiment 5, the placement of a $\lambda/2$ plate and a $\lambda/4$ plate, and the use of a polarization maintaining fiber (a single-mode fiber maintaining the polarization direction of entered light in emitted light) as the single-mode fiber, make it possible to set the polarization state in a sample.

When a wavelength-variable light source is used as the relaxation light source 11, the use of broadband wave plates as the $\lambda/4$ plate 73 and the $\lambda/2$ plate 74, or the use of Berek compensators or Bahinet-Soleil compensators as the $\lambda/4$ plate 73 and the $\lambda/2$ plate 74, makes it possible to set the polarization state in a sample without making component replacement. In this regard, the term "phase plate" is used herein in the sense of including a wave plate or a compensator.

As described above, there can be achieved confocal Raman imaging with high signal-to-noise ratio and high wavenumber resolution by the Raman microscopes of Embodiments 1 to 6. Raman spectra may also be measured by the use of a non-confocal optical system in place of a confocal optical system. Embodiments 1 to 6 as described above may also be used in appropriate combination.

DESCRIPTION OF REFERENCE NUMERALS

11 Relaxation light source
12 Pump light source
13 Mirror
14 Dichroic mirror
15 Dichroic mirror
16 Objective lens
17 Sample
18 Notch filter
19 Notch filter
20 Lens
31 Spatial filter
32 Spectrograph
33 Detector
41 Optical modulator
43 Mirror
44 Dichroic mirror
51 Fiber coupler
52 Fiber cable
53 Fiber coupler
61 Fiber coupler
62 Fiber cable
63 Fiber coupler
64 Fiber cable
65 Fiber combiner
66 Fiber cable
67 Fiber coupler
71 $\lambda/4$ plate
72 $\lambda/2$ plate
73 $\lambda/4$ plate
74 $\lambda/2$ plate

The invention claimed is:

1. A Raman microscope comprising:
a pump light source for emitting pump light as continuous light;
a relaxation light source for emitting relaxation light to induce stimulated emission in a sample;
an optical system for irradiating the relaxation light and the pump light to the sample;
a filter for reducing transmission of the relaxation light and a filter for reducing transmission of the pump light; and
a detector for detecting spontaneous Stokes Raman scattered light generated on a long-wavelength side of the pump light in the sample, wherein both the filters are disposed between the sample and the detector,
wherein the spontaneous Stokes Raman scattered light to be detected has a wavelength different from the relaxation light.

2. The Raman microscope according to claim 1, wherein the wavelength of the relaxation light is within 4000 cm$^{-1}$ on a long-wavelength side from the wavelength of the pump light.

3. The Raman microscope according to claim 1, further comprising a spectrograph for separating the Raman scattered light from light generated in the sample.

4. The Raman microscope according to claim 1, wherein the relaxation light is continuous light.

5. The Raman microscope according to claim 1, further comprising an optical modulator for intensity modulating the relaxation light or the pump light to make filtering of a fluorescence component contained in a signal from the detector.

6. The Raman microscope according to claim 1, wherein the relaxation light and the pump light are irradiated to the sample through a single-mode fiber.

7. The Raman microscope according to claim 6, further comprising:
a first fiber cable into which the pump light is introduced;
a second fiber cable into which the relaxation light is introduced; and
a fiber combiner for combining the first fiber cable and the second fiber cable.

8. The Raman microscope according to claim 1, wherein the relaxation light is introduced into the sample with a dark-field irradiation optical system.

9. The Raman microscope according to claim 1, further comprising at least one of a phase plate into which the pump light is introduced or a phase plate into which the relaxation light is introduced.

10. A Raman spectrometric measuring method comprising the steps of:
emitting pump light as continuous light;
emitting relaxation light to induce stimulated emission in a sample;
irradiating the relaxation light and the pump light to the sample;
reducing transmission of the relaxation light and transmission of the pump light via respective filters; and
subsequently detecting spontaneous Stokes Raman scattered light generated on a long-wavelength side of the pump light in the sample,
wherein the spontaneous Stokes Raman scattered light to be detected has a wavelength different from the relaxation light.

11. The Raman spectrometric measuring method according to claim 10, wherein the wavelength of the relaxation light is within 4000 cm$^{-1}$ on a long-wavelength side from the wavelength of the pump light.

12. The Raman spectrometric measuring method according to claim 10, further comprising the step of spectrally separating the Raman scattered light from light generated in the sample.

13. The Raman spectrometric measuring method according to claim 10, wherein the relaxation light is continuous light.

14. The Raman spectrometric measuring method according to claim 10, wherein the relaxation light or the pump light is intensity modulated; and
a fluorescence component contained in a signal obtained in the above detecting step is removed with a filter.

15. The Raman spectrometric measuring method according to claim 10, wherein the wavelength of the relaxation light is changed to detect a spectrum;
the wavelength of the relaxation light is selected according to the spectrum detected above; and
the relaxation light having the wavelength selected above is irradiated to the sample to detect Raman scattered light in another portion.

16. The Raman spectrometric measuring method according to claim 10, wherein the strength of the relaxation light is changed to detect a spectrum;
the strength of the relaxation light is selected according to the spectrum detected above; and
the relaxation light having the strength selected above is irradiated to the sample to detect Raman scattered light in another portion.

17. The Raman spectrometric measuring method according to claim 10, wherein the relaxation light and the pump light are irradiated to the sample through a single-mode fiber.

18. The Raman spectrometric measuring method according to claim 10, wherein a polarization direction of the relaxation light and a polarization direction of the pump light are made orthogonal or parallel with each other in the sample.

* * * * *